(12) United States Patent
Petersen et al.

(10) Patent No.: US 7,371,863 B2
(45) Date of Patent: May 13, 2008

(54) METHOD FOR MANUFACTURE OF THIP

(75) Inventors: Hans Petersen, Vanløse (DK); Michael Bech Sommer, Bagsvaerd (DK); Robert Dancer, Hvidovre (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/570,551

(22) PCT Filed: Sep. 1, 2004

(86) PCT No.: PCT/DK2004/000579

§ 371 (c)(1),
(2), (4) Date: May 10, 2006

(87) PCT Pub. No.: WO2005/023820

PCT Pub. Date: Mar. 17, 2005

(65) Prior Publication Data

US 2007/0112198 A1 May 17, 2007

Related U.S. Application Data

(60) Provisional application No. 60/500,422, filed on Sep. 5, 2003.

(30) Foreign Application Priority Data

Sep. 5, 2003 (DK) .............................. 2003 01277

(51) Int. Cl.
*C07D 471/02* (2006.01)
*C07D 491/02* (2006.01)
*C07D 498/02* (2006.01)

(52) U.S. Cl. .................................... 546/116

(58) Field of Classification Search .............. 546/116
See application file for complete search history.

(56) References Cited

U.S. PATENT DOCUMENTS 4,353,910 A * 10/1982 Perregaard ................. 514/302

FOREIGN PATENT DOCUMENTS

| DE | 31 45 473 A1 | 8/1982 |
|---|---|---|
| EP | 0 000 338 | 11/1981 |
| EP | 0840601 | 5/1998 |

OTHER PUBLICATIONS

Krogsgaard-Larsen et al., Acta Chemica Scandinavica B, "Muscimol analogues. II. synthesis of some bicyclic 3-isoxazolo Zwitterions", 1977, vol. 31., pp. 584-588.*
Database Registery Online; Chemical Abstracts Service, Colombus, Ohio, US; XP002308640, retrieved from STN, 85118-32-7.
Erminio Costa et al., Trends in Pharmacological Sciences including Toxicological Sciences 1996, 17, pp. 192-200.

* cited by examiner

*Primary Examiner*—Margaret D. Seaman
*Assistant Examiner*—Niloofar Rahmani
(74) *Attorney, Agent, or Firm*—Darby & Darby P.C.

(57) ABSTRACT

The present invention relates to a new method of preparing gaboxadol (THIP), which is useful for treating sleep disorders. In particular a method of preparing THIP comprising reacting a compound of formula (8b) or a salt thereof with an acid, typically a mineral acid, to obtain THIP as an acid addition salt. The present invention also relates to several intermediates (8b)

37 Claims, No Drawings

US 7,371,863 B2

METHOD FOR MANUFACTURE OF THIP

CROSS REFERENCE TO PRIOR APPLICATION

This is a U.S. national phase application under 35 U.S.C. §371 of International Patent Application No. PCT/DK2004/000579, filed Sep. 1, 2004, and claims benefit of Danish Patent Application No. PA 2003 01277, filed Sep. 5, 2003 and U.S. Provisional Application No. 60/500,422, filed Sep. 5, 2003 which is incorporated by reference herein. The International Application was published in English on Mar. 17, 2005 as WO 2005/023820 A1 under PCT Article 21(2).

FIELD OF THE INVENTION

The present invention relates to a new method of manufacturing the compound 4,5,6,7-tetrahydroisoxazolo[5,4-c9]pyridin-3-ol (THIP) having the INN name Gaboxadole, and also to new intermediates, such as isoxazolo[5,4-c]pyridin-3-ol (HIP), used in the method.

BACKGROUND OF THE INVENTION

Receptors for the major inhibitory neurotransmitter, gammaamino butyric acid (GABA), are divided into two main classes: $GABA_A$ receptors which are members of the ligand gated ion channel superfamily; and the $GABA_B$ receptors which are G-protein coupled receptors.

In a number of clinical conditions, hypoactivity of the inhibitory GABA system has been hypothesised as the underlying mechanism of the pathology in question. These conditions include epilepsy, anxiety, stress, sleep disorders and pain. However, although positive modulators of the $GABA_A$ receptor complex, such as benzodiazepines, in a number of circumstances are very effective, there is a general consensus that unselective benzodiazepines produce so many side effects that compounds substituting for presently used drugs are needed (Costa and Guidotto *Trends Pharmacol. Sci.* 1996, 17, 192-200).

The present invention provides non-steroidal and non-benzodiazepine compounds interacting directly with the recognition site at the $GABA_A$ receptor as agonists, which have beneficial effects in disease states relating to reduced neurostoroidal activation.

The diseases, including premenstrual syndrome, postnatal depression and post menopausal related dysphoric disorders, are significantly better treated with $GABA_A$ agonists than with benzodiazepines and neurosteroids which produce tolerance after short term treatment.

The potent GABA agonist 4,5,6,7-tetrahydroisoxazolo[5,4-c9]pyridin-3-ol (THIP) is disclosed in EP 000 338 B1 wherein a method of making the compound is also described. THIP is useful for treating sleep disorders which is disclosed in EP 840601 B1.

Definitions

The term "a" as used herein is intended to mean "one or more" or "at least one", except where it is clear from the text that it means one.

The term "$C_{1-4}$alkyl", "$C_{1-6}$alkyl", or "$C_{1-12}$alkyl" as used herein refers to a branched or unbranched alkyl group having from one to four, one to six, or one to twelve carbon atoms inclusive, respectively, including but not limited to methyl, ethyl, 1-propyl, 2-propyl, 1-butyl, 2-butyl, 2-methyl-2-propyl and 2-methyl-1-propyl.

The term "$C_{1-6}$alkoxy", or "$C_{1-12}$alkoxy" as used herein designate such groups in which the $C_{1-6}$-alkyl or $C_{1-12}$-alkyl is as defined above and is linked via an oxygen, including but not limited to methoxy, ethoxy, 1-propoxy, 1-butoxy.

The term "$C_{2-6}$alkenyl", or "$C_{2-12}$alkenyl" as used herein, respectively, designate such groups having from two to six carbon atoms, or two to twelve carbon atoms, including one double bond respectively, including but not limited to ethenyl, propenyl, and butenyl.

The term "$C_{1-6}$alkylene" as used herein refers to a branched or unbranched alkylene group having from one to six carbon atoms inclusive, including but not limited to methylene, and ethylene.

The term "$C_{3-8}$cycloalkyl" as used herein designates a monocyclic or bicyclic carbocycle having three to eight carbon atoms inclusive, including but not limited to cyclopropyl, cyclopentyl, and cyclohexyl.

The term "$C_{3-8}$cycloalkenyl" as used herein designates a monocyclic or bicyclic carbocycle having three to eight carbon atoms inclusive and including one double bond.

The term "$C_{1-12}$alkyl chloroformate" designate such groups in which the $C_{1-12}$-alkyl, such as $C_{1-6}$-alkyl, is as defined above and is the ester portion of a chloroformate, including but not limited to methyl chloroformate or ethyl chloroformate.

The term "acyl" as used herein refers to formyl, $C_{1-6}$-alk(en/yn)ylcarbonyl, arylcarbonyl, aryl-$C_{1-6}$-alk(en/yn)ylcarbonyl, $C_{3-8}$-cycloalk(en)ylcarbonyl or a $C_{3-8}$-cycloalk(en)yl-$C_{1-6}$-alk(en/yn)yl-carbonyl group.

The expression $C_{1-6}$-alk(en/yn)yl means a $C_{1-6}$-alkyl, $C_{2-6}$-alkenyl or a $C_{2-6}$-alkynyl group. The expression $C_{3-8}$-cycloalk(en)yl means a $C_{3-8}$-cycloalkyl- or cycloalkenyl group.

The term "aryl" as used herein refers to carbocyclic, aromatic systems such as phenyl and naphtyl.

The term "heteroaryl" as used herein refers to 5- to 6-membered aromatic systems containing 1 to 5 carbon atoms and one or more heteroatoms selected from O, S or N, such as 5-membered monocyclic rings such as oxathiazoles, dioxazoles, dithiazoles, oxadiazoles, thiadiazoles, triazoles, isoxazoles, oxazoles, isothiazoles, thiazoles, imidazoles, pyrazoles, pyrroles, furan(s) or thiophene(s), e.g. 3H-1,2,3-oxathiazole, 1,3,2-oxathiazole, 1,3,2-dioxazole, 3H-1,2,3-dithiazole, 1,3,2-dithiazole, 1,2,3-oxadiazole, 1,2,3-thiadiazole, 1H-1,2,3-triazole, isoxazole, oxazole, isothiazole, thiazole, 1H-imidazole, 1H-pyrazole, 1H-pyrrole, furan or thiophene, or 6-membered monocyclic rings such as oxathiazines, dioxazines, dithiazines, oxadiazines, thiadiazines, triazines, oxazines, thiazines, pyrazines, pyridazines, pyrimidines, oxathiins, dioxins, dithiins, pyridines, pyrans or thiins, e.g. 1,2,3-oxathiazine, 1,2,4-oxathiazine, 1,2,5-oxathiazine, 1,4,2-oxathiazine, 1,4,3-oxathiazine, 1,2,3-dioxazine, 1,2,4-dioxazine, 4H-1,3,2-dioxazine, 1,4,2-dioxazine, 2H-1,5,2-dioxazine, 1,2,3-dithiazine, 1,2,4-dithiazine, 4H-1,3,2-dithiazine, 1,4,2-dithiazine, 2H-1,5,2-dithiazine, 2H-1,2,3-oxadiazine, 2H-1,2,4-oxadiazine, 2H-1,2,5-oxadiazine, 2H-1,2,6-oxadiazine, 2H-1,3,4-oxadiazine, 2H-1,2,3-thiadiazine, 2H-1,2,4-thiadiazine, 2H-1,2,5-thiadiazine, 2H-1,2,6-thiadiazine, 2H-1,3,4-thiadiazine, 1,2,3-triazine, 1,2,4-triazine, 2H-1,2-oxazine, 2H-1,3-oxazine, 2H-1,4-oxazine, 2H-1,2-thiazine, 2H-1,3-thiazine, 2H-1,4-thiazine, pyrazine, pyridazine, pyrimidine, 4H-1,3-oxathiin, 1,4-oxathiin, 4H-1,3-dioxin, 1,4-dioxin, 4H-1,3-dithiin, 1,4-dithiin, pyridine, 2H-pyran or 2H-thiin.

The term "acidification" as used herein means that an acid is added to the reaction mixture adjusting the pH to below pH 6.5.

The term "a leaving group" as used herein is a well-known expression to the skilled chemist, examples being halogens, such as Br, Cl, I, or mesylate or tosylate.

The term "a salt" as used herein is intended to mean any salt which a particular compound may form, and is usually intended to comprise acid addition salts, however, the compounds may also form other salts with bases, such as metal salts, eg. sodium salts, and ammonium salts, eg. salts of amines, such as triethylamine.

The term "an acid addition salt" as used herein is intended to mean any acid addition salt which a particular compound may form upon reaction of the compound with the acid in a solvent, as known to the skilled person in the art. Suitable examples are hydrochloric acid, hydrobromic acid, nitric acid, sulfuric acid, phosphoric acid and the like. Other suitable examples are organic salts such as acetic, propionic, glycolic, oxalic, malonic, succinic, citric acid and the like.

The term "a mild reducing agent" as used herein is a well-known expression to the skilled chemist, reference is made to Brown, H. C; Krishnamurthy; *Tetrahedron*, 35, 1979, pp 567-607. Suitable examples are borohydrides.

The term "a nucleophile" as used herein is a well-known expression to the skilled chemist, reference is made to "Advanced Organic Chemistry" ($3^{rd}$ edition), Jerry March, Wiley-Interscience. The term "a soft nucleophile" as used herein is also described in "Advanced Organic Chemistry" ($3^{rd}$ edition), Jerry March, Wiley-Interscience. Suitable examples are Cl$^-$, Br$^-$, I$^-$, or NC—S$^-$.

The term "a dehydrating agent" as used herein is a well-known expression to the skilled chemist, and is intended to cover agents, such as thionylchloride, a chloroformate such as isobutyl chloroformate, or a carbodiimide such as DCI/DCC.

DESCRIPTION OF THE INVENTION

The present invention relates to a new method of manufacturing the compound 4,5,6,7-tetrahydroisoxazolo[5,4-c9]pyridin-3-ol (THIP).

In one aspect the present invention relates to a method of preparing THIP comprising the steps:
a) reacting a compound of formula (2)

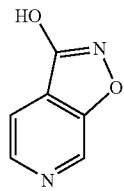
(2)

with an alkylating agent of formula (3)

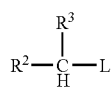
(3)

wherein $R^2$ and $R^3$ are independently selected from H, $C_{1-12}$alkyl, $C_{2-12}$alkenyl, $C_{3-8}$cycloalkyl, $C_{3-8}$cycloalkenyl, acyl, aryl, or heteroaryl, optionally substituted with a $C_{1-12}$alkyl, $C_{1-12}$alkoxy, or aryl; and
L is a leaving group, to obtain a quarternary salt of formula (4)

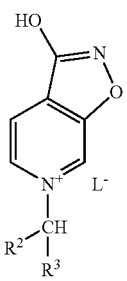
(4)

wherein L, $R^2$ and $R^3$ are as defined above,
b) reacting the quarternary salt of (4) with a mild reducing agent to obtain a compound of formula (5)

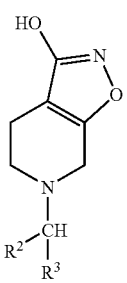
(5)

wherein $R^2$ and $R^3$ are as defined above,
c) reacting a compound of formula (5) with a reagent of formula (6a)

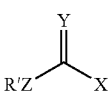
(6a)

wherein R' is $C_{1-12}$alkyl, $C_{2-12}$alkenyl, $C_{3-8}$cycloalkyl, $C_{3-8}$cycloalkenyl, acyl, or aryl optionally substituted with one or more $C_{1-12}$alkyl, $C_{1-12}$alkoxy, or aryl,
X is a leaving group,
Y is O or S,
Z is O, S or $C_{1-6}$alkyl, optionally followed by reaction with a nucleophile, to obtain a mixture of a compound of formula (7a) and a compound of (7b)

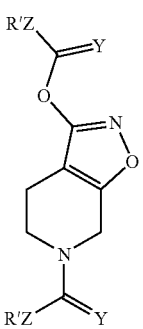
(7a)

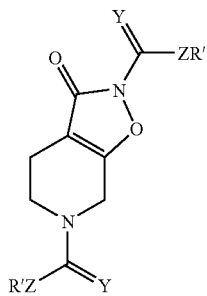
(7b)

wherein Y, Z, and R' are as defined above,
d) reacting the mixture of (7a) and (7b) with a nucleophile, followed by acidification, to obtain a compound of formula (8a)

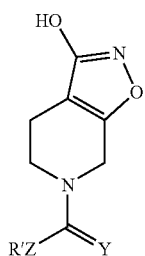
(8a)

wherein Y, Z, and R' are as defined above,
e) reacting a compound of formula (8a) with an acid to obtain THIP as an acid addition salt.

In a further aspect the present invention relates to a method of preparing THIP wherein steps a and b are as above, comprising the further steps:
c2) reacting a compound of formula (5) with a reagent of formula (6b)

(6b)

wherein R is $C_{1-12}$alkyl, $C_{2-12}$alkenyl, $C_{3-8}$cycloalkyl, $C_{3-8}$cycloalkenyl, acyl, or aryl optionally substituted with one or more $C_{1-12}$alkyl, $C_{1-12}$alkoxy, or aryl,
U is N or $CR^1$, wherein $R^1$ is H, or R,
W is O, S or $NR^4$, wherein $R^4$ is H, or R, optionally followed by reaction with a nucleophile, to obtain a mixture of a compound of formula (7c) and a compound of (7d)

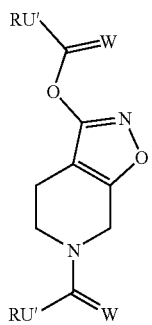
(7c)

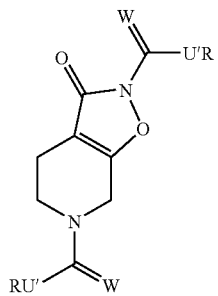
(7d)

wherein R is $C_{1-12}$alkyl, $C_{2-12}$alkenyl, $C_{3-8}$cycloalkyl, $C_{3-8}$cycloalkenyl, acyl, or aryl optionally substituted with one or more $C_{1-12}$alkyl, $C_{1-12}$alkoxy, or aryl,
U' is NH or $CHR^1$, wherein $R^1$ is H, or R,
W is O, S or $NR^4$, wherein $R^4$ is H, or R,
d2) reacting the mixture of (7c) and (7d) with a nucleophile, followed by acidification, to obtain a compound of formula (8b)

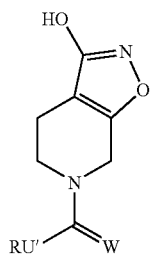
(8b)

wherein W, U', and R are as defined above,
e2) reacting a compound of formula (8b) with an acid to obtain THIP as an acid addition salt.

The compound of formula (2)

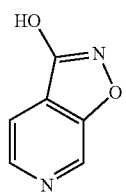
(2)

is novel and may be prepared by the steps comprising:
i) reacting a compound of formula (9)

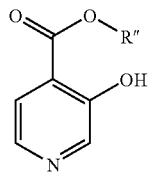
(9)

wherein R" is $C_{1-4}$alkyl (such as methyl, ethyl, n-propyl, n-butyl), with hydroxylamine hydrochloride and a base, such as NaOH, to obtain a compound of formula (10)

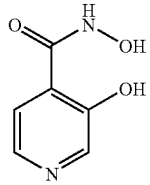

(10)

and ii) reacting the compound of formula (10) with a dehydrating agent to obtain (2).

The base should be strong enough to adjust pH≧9, preferably ≧10.

Typical compounds of formula (9) are methyl and ethyl 3-hydroxy-isonicotinate, which are described in (Contribution No. 240 from the research laboratories of Hoffmann-La Roche Inc.), Synthetic Tuberculostats. II, pages 547-554, by H. Herbert Fox. The compound 3,N-dihydroxy-isonicotinamide (10) is described in Ceskoslov. Farm. 11, 1962, pages 76-79, and in Acta Facultatis Pharmaceuticae Bohemoslovenicae TOM. IV. 1962, pages 65-91.

In a further aspect the present invention relates to a method of preparing the compound of formula (2) comprising reacting the compound of formula (10)

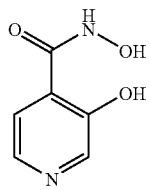

(10)

with a dehydrating agent to obtain (2). In an embodiment the dehydrating agent is selected from thionylchloride, a chloroformate, or a carbodiimide. Typical dehydrating agents are thionylchloride, isobutyl chloroformate, and DCI/DCC.

Accordingly, the present invention also relates to a compound of formula (2)

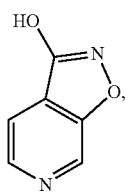

(2)

or a salt thereof. In one embodiment the salt is an acid addition salt, such as a hydrochloric acid, hydrobromic acid, nitric acid, sulfuric acid, or phosphoric acid salt. In another embodiment it is the free base.

In step a of the present method the reaction is typically carried out in an organic solvent. In one embodiment step a is carried out in a polar solvent, such as NMP.

In the alkylating agent of formula (3) $R^2$ and $R^3$ are independently selected from H, $C_{1-12}$alkyl, $C_{1-12}$alkenyl, $C_{3-8}$cycloalkyl, $C_{3-8}$cycloalkenyl, acyl, aryl, or heteroaryl, optionally substituted with a $C_{1-12}$alkyl, $C_{1-12}$alkoxy, or aryl, and L is a leaving group, eg. Br, Cl, I, OMs, or OTs. When $R^2$ and $R^3$ are independently selected from $C_{1-12}$alkyl, $C_{1-12}$alkenyl, $C_{3-8}$cycloalkyl, $C_{3-8}$cycloalkenyl, acyl, aryl, or heteroaryl, each of these substituents may optionally be substituted with a $C_{1-12}$alkyl, $C_{1-12}$alkoxy, or aryl. In a further embodiment one of $R^2$ and $R^3$ is H and the other is as above. Typically, $R^2$ and $R^3$ are independently selected from H, methyl, ethyl, allyl, phenacyl, phenyl or methoxyphenyl. Typically, L is selected from Br, Cl, I, OMs, or OTs. Examples of alkylating agents are selected from MeI, EtD, BzBr, p-$CH_3OC_6H_4CH_2Br$, allylBr, and the corresponding mesylates (OMs) and tosylates (OTs).

In step b of the present method the reaction is carried out in an organic or inorganic solvent, or mixtures thereof. In one embodiment step b is carried out in alcohol and water, such as aqueous ethanol.

Typically, the mild reducing agent in step b is selected from $LiBH_4$ or $NaBH_4$.

In step c one alternative is to react a compound of formula (5) with a reagent of formula (6a)

(6a)

wherein R' is $C_{1-12}$alkyl, $C_{2-12}$alkenyl, $C_{3-8}$cycloalkyl, $C_{3-8}$cycloalkenyl, acyl, or aryl or heteroaryl optionally substituted with one or more $C_{1-12}$alkyl, $C_{1-12}$alkoxy, or aryl, X is a leaving group, Y is O or S, and Z is O, S or $C_{1-6}$alkyl. When Z is $C_{1-6}$alkyl it may be necessary to further react with a nucleophile such as $Cl^-$, $Br^-$, $I^-$, or NC—$S^-$. In one embodiment R' is $C_{1-4}$alkyl, $C_{2-6}$alkenyl, $C_{3-8}$cycloalkyl, $C_{3-8}$cycloalkenyl, acyl, or phenyl optionally substituted with a $C_{1-6}$alkyl, $C_{1-6}$alkoxy, or phenyl, X is selected from Cl, Br, I, Y is O, and Z is O. In particular, the reagent of formula (6a) is selected from $C_{1-12}$alkyl chloroformate, or $C_{1-12}$alkyl chlorothiolformate, typically, $C_{1-6}$alkyl chloroformate, such as methyl chloroformate, ethyl chloroformate, or $C_{1-6}$alkyl chlorothiolformate, such as ethyl chlorothiolformate.

Another alternative in step c is to first protect a compound of formula (5) as a carbonate or carbamate, such as a t-butyl- or 2,2,2-trichloroethylcarbonate/carbamate, and then reacted with the reagent of formula (6a), to obtain a mixture of a compound of formula (7a) and a compound of formula (7b).

In step c2 one alternative is to react a compound of formula (5) with a reagent of formula (6b)

(6b)

wherein R is $C_{1-12}$alkyl, $C_{2-12}$alkenyl, $C_{3-8}$cycloalkyl, $C_{3-8}$cycloalkenyl, acyl, or aryl optionally substituted with one or more $C_{1-12}$alkyl, $C_{1-12}$alkoxy, or aryl, U is N or CR$^1$, wherein R$^1$ is H, or R, W is O, S or NR$^4$, wherein R$^4$ is H, or R, optionally followed by reaction of a nucleophile such as Cl$^-$, Br$^-$, I$^-$, or NC—S$^-$, to obtain a mixture of a compound of formula (7c) and a compound of formula (7d)

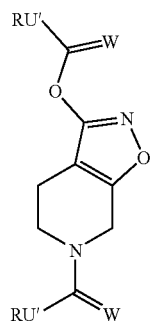
(7c)

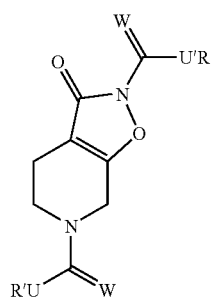
(7d)

wherein U', W, and R are as defined above. In one embodiment R is C$_{1-6}$alkyl, C$_{2-6}$alkenyl, C$_{3-8}$cycloalkyl, C$_{3-8}$cycloalkenyl, acyl, or phenyl optionally substituted with a C$_{1-6}$alkyl, C$_{1-6}$alkoxy, or phenyl, U' is NH or CHR$^1$, wherein R$^1$ is H, C$_{1-6}$alkyl, C$_{2-6}$alkenyl, C$_{3-8}$cycloalkyl, C$_{3-8}$cycloalkenyl, acyl, or phenyl optionally substituted with a C$_{1-6}$alkyl, C$_{1-6}$alkoxy, or phenyl, W is O, S or NR$^4$, wherein R$^4$ is H, C$_{1-6}$alkyl, C$_{2-6}$alkenyl, C$_{3-8}$cycloalkyl, C$_{3-8}$cycloalkenyl, acyl, or phenyl optionally substituted with a C$_{1-6}$alkyl, C$_{1-6}$alkoxy, or phenyl, and the nucleophile is selected from Cl$^-$, Br$^-$, I$^-$, or NC—S$^-$. In particular, the reagent of formula (6b) is selected from an isocyanate such as isopropyl isocyanate or phenyl isocyanate, or an isothiocyanate such as phenyl isothiocyanate, or a ketene.

In step d the mixture of (7a) and (7b) is reacted with a nucleophile, typically a soft nucleophile, followed by acidification, to obtain a compound of formula (8a)

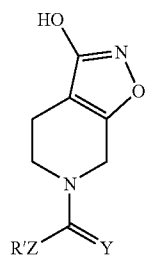
(8a)

wherein Y, Z, and R' are as defined above. In one embodiment the soft nucleophile is ammonia, an amine, a diamine, a thiol, a thiolate, a sulfide in a solvent, such as an aqueous or organic solution. Examples of soft nucleophiles are aqueous ammonia, methylamine, and ethylenediamine. The step of acidification may be performed with an aqueous acid adjusting the pH to ≦5. In further embodiments acidification is performed by adjusting the pH to ≦4, typically ≦3, such as ≦2, eg. pH is about 1. Typically, the aqueous acid is a mineral acid, such as hydrochloric acid, hydrobromic acid, nitric acid, sulfuric acid, or phosphoric acid.

As mentioned above in step d, the nucleophile is in an aqueous or organic solution. Preferably, after reaction with the nucleophile the aqueous phase is separated, followed by acidification as outlined above, and extraction into an organic phase, eg. ethyl acetate. This purification step provides a compound of formula (8a) or a salt thereof in very high purity, typically, more than 98%, such as greater than 99% according to HPLC (such as the Analytical Method HPLC as described below).

In step d2 the mixture of (7c) and (7d) is reacted with a nucleophile, typically a soft nucleophile, followed by acidification, to obtain a compound of formula (8b)

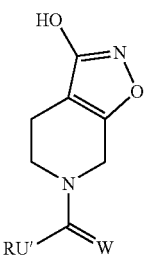
(8b)

wherein U', W, and R are as defined above. In one embodiment the soft nucleophile is ammonia, an amine, a diamine, a thiol, a thiolate, a sulfide in a solvent, such as an aqueous or organic solution. Examples of soft nucleophiles are aqueous ammonia, methylamine, and ethylenediamine. The step of acidification may be performed with an aqueous acid adjusting the pH to ≦5. In further embodiments acidification is performed by adjusting the pH to ≦4, typically ≦3, such as ≦2, eg. pH is about 1. Typically, the aqueous acid is a mineral acid, such as hydrochloric acid, hydrobromic acid, nitric acid, sulfuric acid, or phosphoric acid.

As mentioned above in step d (or d2), the nucleophile is in an aqueous or organic solution. Preferably, after reaction with the nucleophile the aqueous phase is separated, followed by acidification as outlined above, and extraction into an organic phase, eg. ethyl acetate. This purification step provides a compound of formula (8a) (or (8b)) or a salt thereof in very high purity, typically, more than 98%, such as greater than 99% according to HPLC (such as the Analytical Method HPLC as described below).

In step e (or e2) a compound of formula (8a) (or (8b)) or a salt thereof is reacted with an acid, typically a mineral acid, to obtain THIP as an acid addition salt. The reaction is typically carried out in an organic solvent, such as an organic carboxylic acid, eg. acetic acid. Examples of suitable mineral acids are hydrochloric acid, hydrobromic acid, nitric acid, sulfuric acid, or phosphoric acid.

Accordingly, a further aspect of the present invention relates to a method of preparing THIP comprising reacting a compound of formula (8a) or a salt thereof

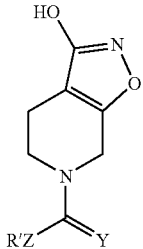

(8a)

wherein R' is $C_{1-12}$alkyl, $C_{2-12}$alkenyl, $C_{3-8}$cycloalkyl, $C_{3-8}$cycloalkenyl, acyl, or aryl optionally substituted with one or more $C_{1-12}$alkyl, $C_{1-12}$alkoxy, or aryl,
Y is O or S, and
Z is O, S or $C_{1-6}$alkyl, with an acid, typically a mineral acid, to obtain THIP as an acid addition salt. The reaction is typically carried out in an organic solvent, such as an organic carboxylic acid, eg. acetic acid. Examples of suitable mineral acids are hydrochloric acid, hydrobromic acid, nitric acid, sulfuric acid, or phosphoric acid.

Since a compound of formula (8a) is a useful intermediate in the preparation of THIP, it is a further aspect of the present invention.

Thus, the present invention relates to compound of formula (8a)

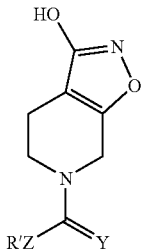

(8a)

wherein R' is $C_{1-12}$alkyl, $C_{2-12}$alkenyl, $C_{3-8}$cycloalkyl, $C_{3-8}$cycloalkenyl, acyl, or aryl optionally substituted with one or more $C_{1-12}$alkyl, $C_{1-12}$alkoxy, or aryl,
Y is O or S,
Z is O, S or $C_{1-6}$alkyl, or a salt thereof. In one embodiment R' is $C_{1-6}$alkyl, $C_{2-4}$alkenyl, $C_{3-8}$cycloalkyl, $C_{3-8}$cycloalkenyl, acyl, or phenyl optionally substituted with a $C_{1-4}$alkyl, $C_{1-4}$alkoxy, or phenyl. In another embodiment Y is O. In another embodiment Z is O. In a further embodiment Y and Z are both O, and R' is selected from any one of the above substituents such as $C_{1-6}$alkyl, or benzyl.

Furthermore, a further aspect of the present invention relates to a method of preparing THIP comprising reacting a compound of formula (8b) or a salt thereof

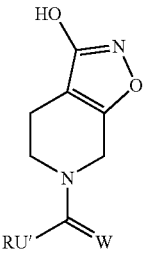

(8b)

wherein R is $C_{1-12}$alkyl, $C_{2-12}$alkenyl, $C_{3-8}$cycloalkyl, $C_{3-8}$cycloalkenyl, acyl, or aryl optionally substituted with one or more $C_{1-12}$alkyl, $C_{1-2}$alkoxy, or aryl,
U' is NH or $CHR^1$, wherein $R^1$ is H, $C_{1-6}$alkyl, $C_{2-6}$alkenyl, $C_{3-8}$cycloalkyl, $C_{3-8}$cycloalkenyl, acyl, or phenyl optionally substituted with a $C_{1-6}$alkyl, $C_{1-6}$alkoxy, or phenyl,
W is O, S or $NR^4$, wherein $R^4$ is H, $C_{1-6}$alkyl, $C_{2-6}$alkenyl, $C_{3-8}$cycloalkyl, $C_{3-8}$cycloalkenyl, acyl, or phenyl optionally substituted with a $C_{1-6}$alkyl, $C_{1-6}$alkoxy, or phenyl, with an acid, typically a mineral acid, to obtain THIP as an acid addition salt. The reaction is typically carried out in an organic solvent, such as an organic carboxylic acid. Examples of suitable mineral acids are hydrochloric acid, hydrobromic acid, nitric acid, sulfuric acid, or phosphoric acid.

Since a compound of formula (8b) is a useful intermediate in the preparation of THIP, it is a further aspect of the present invention.

Thus, the present invention relates to compound of formula (8b)

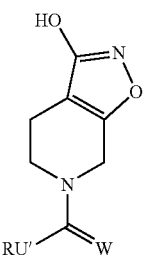

(8b)

wherein R is $C_{1-12}$alkyl, $C_{2-12}$alkenyl, $C_{3-8}$cycloalkyl, $C_{3-8}$cycloalkenyl, acyl, or aryl optionally substituted with one or more $C_{1-12}$alkyl, $C_{1-12}$alkoxy, or aryl,
U' is NH or $CHR^1$, wherein $R^1$ is H, $C_{1-6}$alkyl, $C_{2-6}$alkenyl, $C_{3-8}$cycloalkyl, $C_{3-8}$cycloalkenyl, acyl, or phenyl optionally substituted with a $C_{1-6}$-alkyl, $C_{1-6}$alkoxy, or phenyl,
W is O, S or $NR^4$, wherein $R^4$ is H, $C_{1-6}$alkyl, $C_{2-6}$alkenyl, $C_{3-8}$cycloalkyl, $C_{3-8}$cycloalkenyl, acyl, or phenyl optionally substituted with a $C_{1-6}$alkyl, $C_{1-6}$alkoxy, or phenyl, or a salt thereof. In one embodiment R is $C_{1-6}$alkyl, $C_{2-6}$alkenyl, $C_{3-8}$cycloalkyl, $C_{3-8}$cycloalkenyl, acyl, or phenyl optionally substituted with a $C_{1-6}$alkyl, $C_{1-6}$alkoxy, or phenyl. In another embodiment W is O or S. In a further embodiment W is $NR^4$, wherein $R^4$ is H, $C_{1-6}$alkyl, $C_{2-6}$alkenyl, $C_{3-8}$cycloalkyl, $C_{3-8}$cycloalkenyl, acyl, or phenyl optionally substituted with a $C_{1-6}$alkyl, $C_{1-6}$alkoxy, or phenyl. In a further embodiment U' is NH.

Experimental Part

The following examples are meant to illustrate various embodiments of the invention and should not be read as limiting the scope of protection.

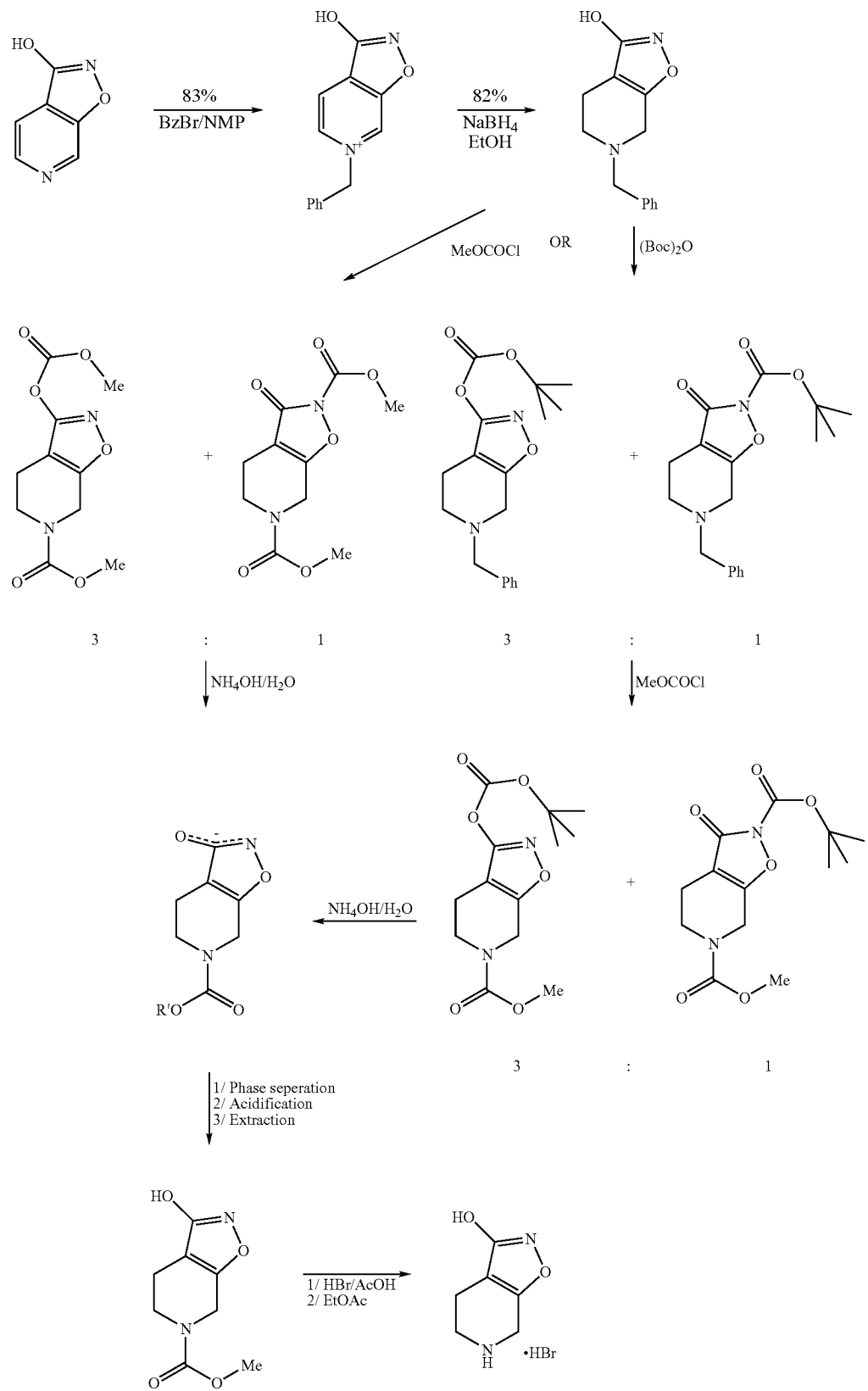

Analytical Method HPLC

HPLC analyses are performed according to the procedures described below.

| | |
|---|---|
| Instrument Varian ProStar System | Pump Model 230 |
| | Detector UV Model 310 |
| | Autosampler/Column Oven Model 410 |
| | Star Chromatography Workstation |
| | Software V. 5.5 |
| Detector | UV 220 nm |
| Column | Merck LiChrosorb RP8 250 × 4 mm, 5 µm |
| Column Temperature | 35° C. |
| Mobile Phase | Water/Acetonitrile 50:50; buffered to pH = 3 using $H_3PO_4$/$NEt_3$ |
| Flow | 1.0 mL/min |
| Volume injected | 10 µl |
| Run time | 10 min |
| Gradient | No Gradient; Isocratic |

Standard Preparation

To a small sample (0.1<mg<1.0) was added ca. 1.2 mL mobile phase, and the sample was shaken until dissolution was complete.

Analytical Procedure

The sample was injected, and the area of the desired peak was measured, as was the total area. The product assay was calculated with the formula:

Assay %=Sample Area/Total Area.

In example A below is described a method of preparing the intermediate isoxazolo[5,4-c]pyridin-3-ol (HIP)

EXAMPLE A

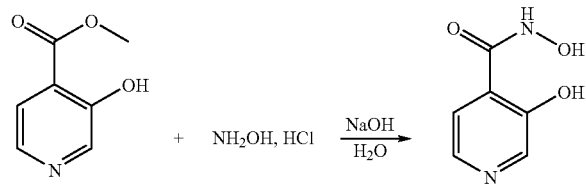

3,N-Dihydroxy-isonicotinamide

To a stirred suspension of methyl 3-hydroxy-isonicotinate (176 g; 1.15 mol) in water/ice (50/50, 1700 mL), was added hydroxylamine hydrochloride (127.9 g; 1.84 mol). The temperature fell to −5° C. and then aqueous NaOH solution (454 mL, 28% w/v) was added dropwise keeping the temperature below 5° C. during the addition. Hereafter the reaction mixture was stirred at ambient temperature for 1.5 h followed by heating to 60° C. At this temperature the pH was adjusted to 5.4 by the addition of aqueous hydrochloric acid (10 M) at which point a heavy precipitate forms. The reaction mixture was then stirred at ambient temperature followed by cooling to 5° C. The pH was then adjusted to 4.0 by the addition of aqueous hydrochloric acid (10 M), and then was stirred whilst cold for 1.5 h. The crystals were filtered off, rinsed with water (3×100 mL), dried on the filter and then dried further at reduced pressure and 40° C. overnight to give 3,N-dihydroxy-isonicotinamide (169.3 g, 96%; HPLC purity 98%) as a white solid.

NMR data: $^1$H-NMR (DMSO-d6, 250 MHz) δ=7.55 (1H, d, J=6 Hz); 8.11 (1H, d, J=6 Hz); 8.32 (1H, s); 9.56 (1H, s, broad peak); 11.50 (1H, s, broad peak) ppm.

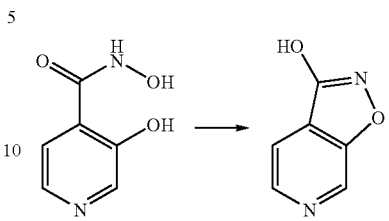

Isoxazolo[5,4-c]pyridin-3-ol (HIP)

Method A

To a stirred suspension of 3,N-dihydroxy-isonicotinamide (50 g; 0.32 mol) in DMF (300 mL), cooled on a water bath at ambient temperature, was added carbonyldiimidazole (DCI) (66.4 g; 0.41 mol. The reaction was stirred over night at ambient temperature.

The next day the solvent was removed under reduced pressure at 70° C. and the residue was dissolved in water and cooled on ice. The pH of the solution (≅7.5) was adjusted to 4.5 by the addition of an aqueous solution of hydrochloric acid (ca. 65 mL, 10 M). The desired product crystallised heavily from the solution. The slurry was evaporated to ca. ⅔ volume to remove traces of DMF, cooled on ice for a couple of hours and filtered. The crystals so obtained were rinsed twice with water and twice with ethanol and dried under reduced pressure at 60° C. overnight to give isoxazolo [5,4-c]pyridin-3-ol (41.7 g, 96%; HPLC purity >99%) as a white solid.

NMR data: $^1$H-NMR (DMSO-d6, 250 MHz) δ=7.84 (1H, d, J=6 Hz), 8.53 (1H, d, J=6 Hz), 9.08 (1H, s) ppm.

Method B

A suspension of 3,N-dihydroxy-isonicotinamide (168 g; 1.09 mol) in pyridine (1600 mL) that had been vigorously stirred for 15 min. to ensure an even suspension, was cooled on an ice-bath to 5° C. Thionylchloride (241 g; 2.03 mol) was added dropwise over 1 hour whilst maintaining the temperature below 10° C. and the reaction was checked for unreacted starting material by means of the hydroxamic acid test (5% $FeCl_3$ in 1M HCl was added to a reaction sample in ethanol, a magenta colour was produced if hydroxamic acid was present). After the addition was complete the cooling bath was removed and the reaction was allowed to warm up to ambient temperature over 1 hour. The reaction mixture was poured into 2 kg of ice/water with vigorous stirring and the pH was adjusted to 3 with concentrated aqueous hydrochloric acid (ca. 1.1 L, 10 M). The title compound crystallized out and the mixture was stirred on an ice-bath for 2 hours. The mixture was filtered and the residue was washed with water, ethanol and diethyl ether and dried under reduced pressure at 60° C. overnight to give isoxazolo [5,4-c]pyridin-3-ol (123 g, 83%; HPLC purity 98%) as a white solid.

NMR data: $^1$H-NMR (DMSO-d6, 250 MHz) δ=7.84 (1H, d, J=6 Hz), 8.53 (1H, d, J=6 Hz), 9.08 (1H, s) ppm.

EXAMPLE 1

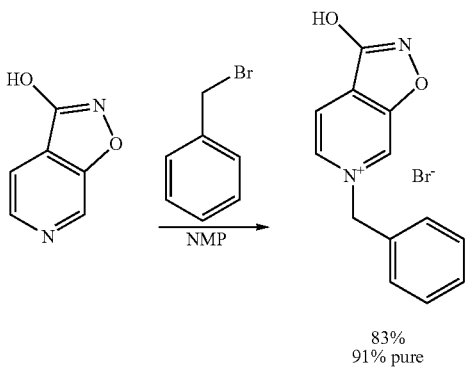

83%
91% pure

6-Benzyl-3-hydroxy-isoxazolo[5,4-c]pyridin-6-ium bromide

To a stirred solution of isoxazolo[5,4-c]pyridin-3-ol (50.0 g, 367 mmol) in NMP (100 ml) was added benzyl bromide (75.4 g, 441 mmol) dropwise rapidly. The thick solution was stirred for 24 h. The mixture was then added slowly to acetone (1.5 L) with stirring, and the solution was seeded. Stirring was continued at room temperature for 30 min, and then for a further 1 h in an ice/water bath. The mixture was filtered, the residue was washed with acetone and then dried under vacuum to give 6-benzyl-3-hydroxy-isoxazolo[5,4-c]pyridin-6-ium bromide (94.1 g, 83%; HPLC: 91% pure) as a white crystalline solid.

NMR data: $^1$H-NMR (DMSO-d6, 500 MHz) δ=6.03 (2H, s), 7.4-7.5 (3H, m), 7.6 (2H, m), 8.54 (1H, d, J=6 Hz), 9.03 (1H, d, J=6 Hz), 10.15 (1H, s) ppm.

EXAMPLE 2

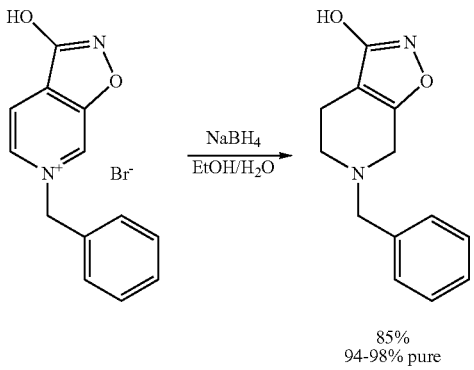

85%
94-98% pure

6-Benzyl-4,5,6,7-tetrahydro-isoxazolo[5,4-c]pyridin-3-ol

To a stirred solution of 6-benzyl-3-hydroxy-isoxazolo[5,4-c]pyridin-6-ium bromide (93 g, 303 mmol) in ethanol/water (500 mL/500 mL) was added NaBH$_4$ (18.66 g, 494 mmol) cautiously portionwise, keeping the temperature under 35° C. (caution! Foams on addition!). The mixture was stirred for 24 h. The mixture was filtered, and the residue was washed with water. The combined filtrates were evaporated under reduced pressure until all of the ethanol had evaporated. A solid began to precipitate, and so the mixture was cooled in an ice-water bath with stirring for 30 min. The solution was filtered, and the residue was washed with cold water. The residue was dried to give 6-benzyl-4,5,6,7-tetrahydro-isoxazolo[5,4-c]pyridin-3-ol (48.6 g, 70%; HPLC 94% pure) as a yellowish solid. After some further evaporation of the combined mother liquors, a second crop gave a further 10.3 g (HPLC: 97.7% pure).

NMR data: $^1$H-NMR (DMSO-d6, 500 MHz) δ=2.3 (2H, t, J=6 Hz), 2.67 (2H, t, J=6 Hz), 3.45 (2H, s), 3.7 (2H, s), 7.2-7.4 (5H, m), 11.3 (1H, bs) ppm.

EXAMPLE 3

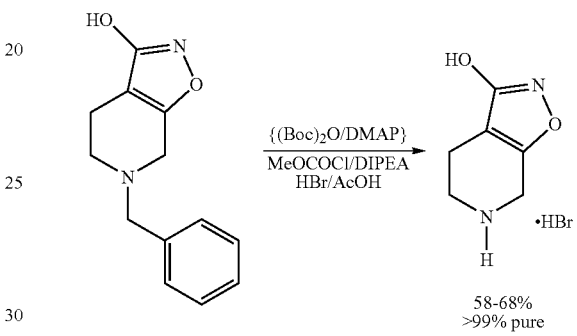

58-68%
>99% pure

4,5,6,7-Tetrahydro-isoxazolo[5,4-c]pyridin-3-ol hydrobromide

Method A

To a stirred solution of 6-benzyl-4,5,6,7-tetrahydro-isoxazolo[5,4-c]pyridin-3-ol (11.5 g, 50 mmol) and DMAP (0.61 g, 5 mmol) in ethyl acetate (100 mL) under a nitrogen atmosphere was added a solution of (Boc)$_2$O (16.4 g, 75 mmol) in ethyl acetate (20 mL). After 30 min was added DIPEA (4.35 mL, 25 mmol) and methyl chloroformate (7.73 mL, 100 mmol), and the mixture was stirred for 48 h. the mixture was cooled in an ice-water bath, and an aqueous solution of ammonia (25% w/v, 120 mL) was added. After 15 minutes the aqueous phase was separated, and was adjusted to pH 1.0 by the addition of aqueous hydrochloric acid (10 M). This aqueous phase was extracted twice with ethyl acetate, and these combined extracts were dried over anhydrous magnesium sulfate and evaporated under reduced pressure. The residue was dissolved in a solution of gaseous HBr in acetic acid (33% w/v, 30 mL), and the mixture was stirred at 40° C. for 6 hours. The mixture was then cooled in an ice-water bath, and ethanol (90 mL) was added. A precipitate formed, and the mixture was stirred in the cold for a further 1 h. The mixture was filtered, and the reside was washed with cold ethanol and dried to give 4,5,6,7-tetrahydro-isoxazolo[5,4-c]pyridin-3-ol hydrobromide (6.4 g, 58%; HPLC >99% pure) as a white solid.

Method B

To a stirred solution of 6-benzyl-4,5,6,7-tetrahydro-isoxazolo[5,4-c]pyridin-3-ol (2.3 g, 10 mmol) in ethyl acetate (25 mL) under a nitrogen atmosphere was added DIPEA (2.6 mL, 15 mmol) and methyl chloroformate (2.7 mL, 35 mmol), and the mixture was stirred for 48 h. the mixture was cooled in an ice-water bath, and an aqueous solution of ammonia (25% w/v, 30 mL) was added. After 15 minutes the aqueous phase was separated, and was adjusted to pH 1.0 by the addition of aqueous hydrochloric acid (10 M). This aqueous phase was extracted twice with ethyl acetate, and these combined extracts were dried over anhydrous magnesium sulfate and evaporated under reduced pressure. The residue was dissolved in a solution of gaseous HBr in acetic acid (33% w/v, 6.3 mL), and the mixture was stirred at 40° C. for 6 hours. The mixture was then cooled in an ice-water bath, and ethanol (25 mL) was added. A precipitate formed, and the mixture was stirred in the cold for a further 1 h. The mixture was filtered, and the reside was washed with cold ethanol and dried to give 4,5,6,7-tetrahydro-isoxazolo[5,4-c]pyridin-3-ol hydrobromide (1.35 g, 58%; HPLC >99% pure) as a white solid. A further crop gave a further 0.15 g, bringing the total yield up to 68% (HPLC: >99% pure).

NMR data: $^1$H-NMR (DMSO-d6, 500 MHz) δ=2.6 (2H, t, J=6 Hz), 3.35 (2H, t, J=6 Hz), 4.3 (2H, s), 9.5 (ca. 2H, bs), ca. 11.6 (ca. 1H, bs) ppm.

We claim:

1. A method of preparing 4,5,6,7-tetrahydroisoxazolo[5,4-c]pyridin-3-ol comprising the steps:

a) reacting a compound of formula (2)

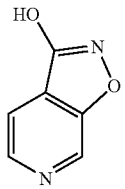

(2)

with an alkylating agent of formula (3)

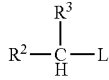

(3)

wherein $R^2$ and $R^3$ are independently selected from H, $C_{1-12}$ alkyl, $C_{2-12}$ alkenyl, $C_{3-8}$ cycloalkyl, $C_{3-8}$ cycloalkenyl, acyl, aryl, or heteroaryl, optionally substituted with a $C_{1-12}$ alkyl, $C_{1-12}$ alkoxy, or aryl, and L is a leaving group, to obtain a quarternary salt of formula (4)

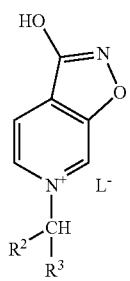

(4)

wherein L, $R^2$ and $R^3$ are as defined above, b) reacting the quarternary salt of formula (4) with a mild reducing agent to obtain a compound of formula (5)

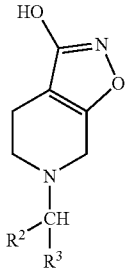

(5)

wherein $R^2$ and $R^3$ are as defined above, c) reacting a compound of formula (5) with a reagent of formula (6a)

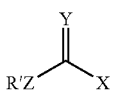

(6a)

wherein R' is $C_{1-12}$ alkyl, $C_{2-12}$ alkenyl, $C_{3-8}$ cycloalkyl, $C_{3-8}$ cycloalkenyl, acyl, or aryl optionally substituted with one or more $C_{1-12}$ alkyl, $C_{1-12}$ alkoxy, or aryl, X is a leaving group, Y is O or S, Z is O, S or $C_{1-6}$ alkyl, optionally followed by reaction with a nucleophile, to obtain a mixture of a compound of formula (7a) and a compound of formula (7b)

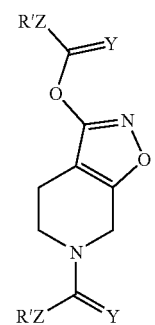

(7a)

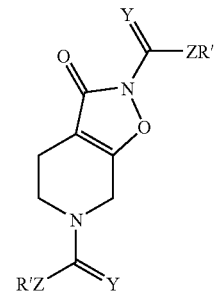

(7b)

wherein Y, Z, and R' are as defined above, d) reacting the mixture of (7a) and (7b) with a nucleophile, followed by acidification, to obtain a compound of formula (8a)

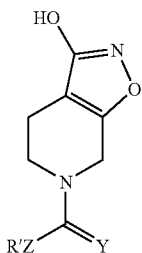

(8a)

wherein Y, Z, and R' are as defined above, and c) reacting a compound of formula (8a) with an acid to obtain 4,5,6,7-tetrahydroisoxazolo[5,4-c]pyridin-3-ol as an acid addition salt.

2. The method of claim 1 wherein step a) is carried out in a polar solvent.

3. The method of claim 1, wherein in the alkylating agent of formula (3), $R^2$ and $R^3$ are independently selected from H, methyl, ethyl, allyl, phenacyl, phenyl, or methoxyphenyl and L is selected from Br, Cl, I, OMs, or OTs.

4. The method of claim 3, wherein the alkylating agent of formula (3) is selected from MeI, EtI, BzBr, p-$CH_3OC_6H_4CH_2Br$, allylBr, and the corresponding mesylates (OMs) and tosylates (OTs).

5. The method of claim 1 wherein the reduction in step b) is carried out in alcohol and water.

6. The method of claim 1 wherein the mild reducing agent in step b) is $LiBH_4$ or $NaBH_4$.

7. The method of claim 1, wherein in the reagent of formula (6a), R' is $C_{1-12}$ alkyl, $C_{2-12}$ alkenyl, $C_{3-8}$ cycloalkyl, $C_{3-8}$ cycloalkenyl, acyl, or aryl optionally substituted with a $C_{1-12}$ alkyl, $C_{1-12}$ alkoxy, or aryl, X is selected from Cl, Br, I, Y is O or S, Z is O or S.

8. The method of claim 7, wherein the reagent of formula (6a) is selected from $C_{1-12}$ alkyl chloroformate.

9. The method of claim 1, wherein a compound of formula (5) is first protected as a carbonate or carbamate and then reacted with the reagent of formula (6a) in step c).

10. The method of claim 1, wherein the nucleophile in step d) is a soft nucleophile in an aqueous or organic solution.

11. The method of claim 1, wherein the reaction with a nucleophile in step d) is followed by acidification by adjusting pH to $\leq 5$.

12. The method of claim 1, wherein in step d), reaction with the nucleophile in an aqueous solution is followed by separating the aqueous phase, followed by acidification with an aqueous acid, and extraction into an organic phase.

13. The method of claim 1, wherein, prior to step e), a compound of formula (Sa) or a salt thereof is purified by a process of extraction from one phase to another.

14. The method of claim 1, wherein in step d) a compound of formula (8a) is obtained at a purity of more than 98% according to HPLC.

15. The method of claim 1, wherein step e) is carried out using a mineral acid.

16. A method of preparing a compound of formula (2)

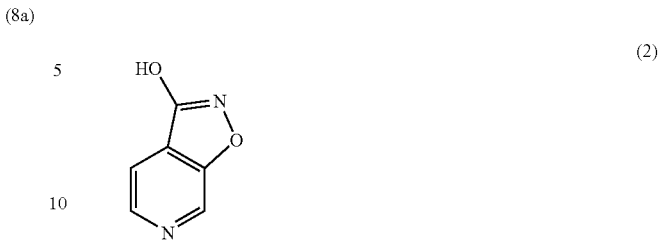

comprising reacting the compound of formula (10)

with a dehydrating agent, to obtain the compound of formula (2).

17. A compound of formula (2)

or a salt thereof.

18. A method of preparing 4,5,6,7-tetrahydroisoxazolo[5,4-c]pyridin-3-ol comprising reacting a compound of formula (8a) or a salt thereof

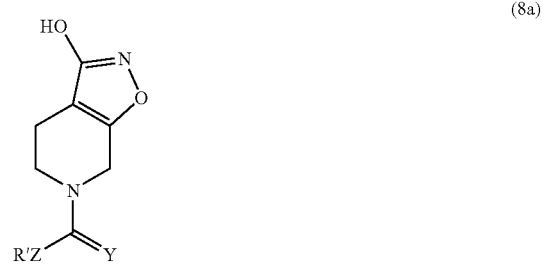

wherein R' is $C_{2-12}$ alkenyl, $C_{3-8}$ cycloalkyl, $C_{3-8}$ cycloalkenyl, acyl, or aryl optionally substituted with one or more $C_{1-12}$ alkyl, $C_{1-12}$ alkoxy, or aryl, Y is O or S, and Z is O, S or $C_{1-6}$ alkylene, with an acid to obtain 4,5,6,7-tetrahydroisoxazolo[5,4-c] pyridin-3-ol as an acid addition salt.

19. A compound of formula (8a)

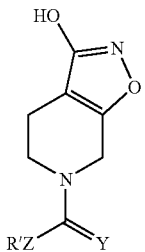
(8a)

wherein R' is C$_{2-12}$ alkenyl, C$_{3-8}$ cycloalkyl, C$_{3-8}$ cycloalkenyl, acyl, or aryl optionally substituted with one or more C$_{1-12}$ alkyl, C$_{1-12}$ alkoxy, or aryl, Y is O or S, Z is O, S or C$_{1-6}$ alkyl, or a salt thereof.

20. A method of preparing 4,5,6,7-tetrahydroisoxazolo[5,4-C]pyridin-3-ol comprising the steps:

a) reacting a compound of formula (2)

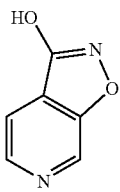
(2)

with an alkylating agent of formula (3)

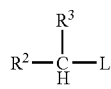
(3)

wherein R$^2$ and R$^3$ are independently selected from H, C$_{1-12}$ alkyl, C$_{2-12}$ alkenyl, C$_{3-8}$ cycloalkyl, C$_{3-8}$ cycloalkenyl, acyl, aryl, or heteroaryl, optionally substituted with a C$_{1-12}$ alkyl, C$_{1-12}$ alkoxy, or aryl, and L is a leaving group, to obtain a quarternary salt of formula (4)

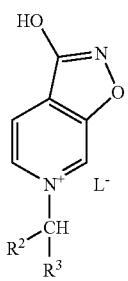
(4)

wherein L, R$^2$ and R$^3$ are as defined above, b) reacting the quarternary salt of formula (4) with a mild reducing agent to obtain a compound of formula (5)

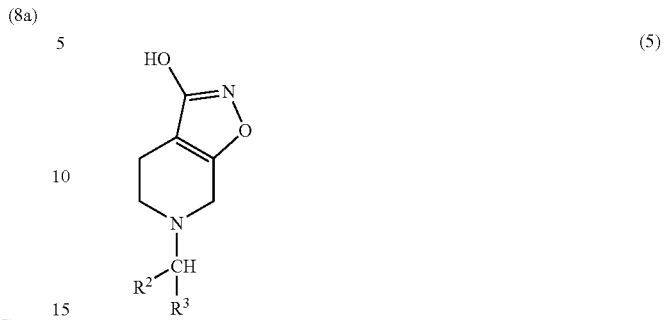
(5)

wherein R$^2$ and R$^3$ are as destined above, c2) reacting the compound of formula (5) with a reagent of formula (6b)

(6b)

wherein R is C$_{1-12}$ alkyl, C$_{2-12}$ alkenyl, C$_{3-8}$ cycloalkyl, C$_{3-8}$ cycloalkenyl, acyl, or aryl optionally substituted with one or more C$_{1-12}$ alkyl, C$_{1-12}$ alkoxy, or aryl, U is N or CR$^1$, wherein R$^1$ is H or R, W is O, S or NR$^4$, wherein R$^4$ is H or R, optionally followed by reaction with a nucleophile, to obtain a mixture of a compound of formula (7c) and a compound of formula (7d)

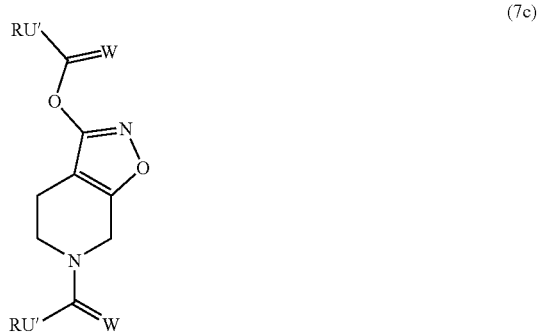
(7c)

(7d)

wherein R is C$_{1-12}$ alkyl, C$_{2-12}$ alkenyl, C$_{3-8}$ cycloalkyl, C$_{3-8}$ cycloalkenyl, acyl, or aryl optionally substituted with one or more C$_{1-12}$ alkyl, C$_{1-12}$ alkoxy, or aryl, U' is N or CR$^1$, wherein R$^1$ is H or R, W is O, S or NR$^4$, wherein R$^4$ is H or R, d2) reacting the mixture of (7c) and (7d) with a nucleophile, followed by acidification, to obtain a compound of formula (8b)

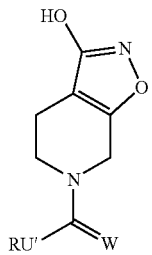

(8b)

wherein W, U', and R are as defined above, e2) reacting a compound of formula (8b) with an acid to obtain 4,5,6,7,-tetrahydroisoxazolo[5,4-c]pyridin-3-ol as an acid addition salt.

21. The method of claim 20 wherein step a) is carried out in a polar solvent.

22. The method of claim 20, wherein in the alkylating agent of formula (3), $R^2$ and $R^3$ are independently selected from H, methyl, ethyl, allyl, phenacyl, phenyl, or methoxyphenyl and L is selected from Br, Cl, I, OMs, or OTs.

23. The method of claim 22, wherein the alkylating agent of formula (3) is selected from MeI, EtI, BzBr, p-$CH_3OC_6H_4CH_2Br$, allylBr, and the corresponding mesylates (OMs) and tosylates (OTs).

24. The method of claim 20 wherein the reduction in step b) is carried out in alcohol and water.

25. The method of claim 20 wherein the mild reducing agent in step b) is $LiBH_4$ or $NaBH_4$.

26. The method of claim 20, wherein in the reagent of formula (6b), R is $C_{1-6}$ alkyl, $C_{2-6}$ alkenyl, $C_{3-8}$ cycloalkyl, $C_{3-8}$ cycloalkenyl, acyl, or phenyl optionally substituted with a $C_{1-6}$ alkyl, $C_{1-6}$ alkoxy, or phenyl, U is N or $CR^1$, wherein $R^1$ is H, $C_{1-6}$ alkyl, $C_{2-6}$ alkenyl, $C_{3-8}$ cycloalkyl, $C_{3-8}$ cycloalkenyl, acyl, or phenyl optionally substituted with a $C_{1-6}$ alkyl, $C_{1-6}$ alkoxy, or phenyl, W is O, S or $NR^4$, wherein $R^4$ is H, $C_{1-6}$ alkyl, $C_{2-6}$ alkenyl, $C_{3-8}$ cycloalkyl, $C_{3-8}$ cycloalkenyl, acyl, or phenyl optionally substituted with a C,6 alkyl, C16 alkoxy, or phenyl.

27. The method of claim 20, wherein the nucleophile is selected from $Cl^-$, $Br^-$, $I^-$, or NC—$S^-$.

28. The method of claim 26, wherein the reagent of formula (6b) is selected from an isocyanate, an isothiocyanate, or a ketene.

29. The method of claim 20, wherein a compound of formula (5) is first protected as a carbonate or carbamate and then reacted with the reagent of formula (6b) in step c2).

30. The method of claim 20, wherein the nucleophile in step d2) is a soft nucleophile in an aqueous or organic solution.

31. The method of claim 20, wherein the reaction with a nucleophile in step d2) is followed by acidification by adjusting pH to $\leq 5$.

32. The method of claim 20, wherein in step d2), reaction with the nucleophile in an aqueous solution is followed by separating the aqueous phase, followed by acidification with an aqueous acid, and extraction into an organic phase.

33. The method of claim 20, wherein, prior to step e2), a compound of formula (8b) or a salt thereof is purified by the process of extraction from one phase to another.

34. The method of claim 20, wherein in step d2), a compound of formula (8b) is obtained at a purity of more than 98% according to HPLC.

35. The method of claim 20, wherein step e2) is carried out using a mineral acid.

36. A method of preparing 4,5,6,7-tetrahydroisoxazolo[5,4-c]pyridin-3-ol comprising reacting a compound of formula (8b) or a salt thereof

(8b)

wherein, R is $C_{1-12}$ alkyl, $C_{2-12}$ alkenyl, $C_{3-8}$ cycloalkyl, $C_{3-8}$ cycloalkenyl, acyl, or aryl optionally substituted with one or more $C_{1-12}$ alkyl, $C_{1-12}$ alkoxy, or aryl, U' is NH or $CHR^1$, wherein $R^1$ is H or R, W is O, S or $NR^4$, wherein $R^4$ is H or R, with an acid to obtain 4,5,6,7-tetrahydroisoxazolo[5,4-c]pyridin-3-ol as an acid addition salt.

37. A compound of formula (8b)

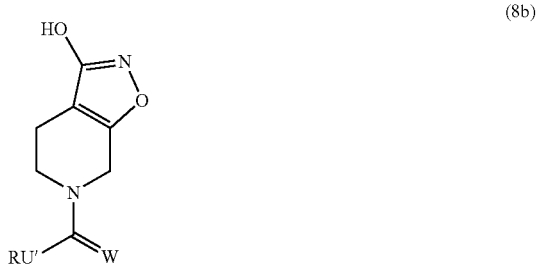

(8b)

wherein R is $C_{1-12}$ alkyl, $C_{2-12}$ alkenyl, $C_{3-8}$ cycloalkyl, $C_{3-8}$ cycloalkenyl, acyl, or aryl optionally substituted with one or more $C_{1-12}$ alkyl, $C_{1-12}$ alkoxy, or aryl, U' is NH or $CHR^1$, wherein $R^1$ is H or R, W is O, S or $NR^4$, wherein $R^4$ is H or R, or a salt thereof.

* * * * *